(12) United States Patent
Hänninen et al.

(10) Patent No.: US 6,310,354 B1
(45) Date of Patent: *Oct. 30, 2001

(54) METHOD AND A DEVICE FOR MONITORING NUCLEIC ACID AMPLIFICATION REACTIONS

(75) Inventors: Pekka Hänninen, Turku (FI); Erkki Soini, Krypingintie 20, FIN-21610 Kirjala (FI)

(73) Assignee: Erkki Soini, Kirjala (FI)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/352,372

(22) Filed: Jul. 13, 1999

Related U.S. Application Data

(63) Continuation-in-part of application No. 09/297,578, filed on May 5, 1999.

(30) Foreign Application Priority Data

Dec. 3, 1996 (FI) .......................................... 964826
Apr. 17, 1997 (FI) .......................................... 971626

(51) Int. Cl.$^7$ ................................................ G01N 33/543
(52) U.S. Cl. ..................................... 250/458.1; 435/288.7
(58) Field of Search ............................ 250/458.1, 459.1, 250/461.1, 462.2; 435/288.7; 422/82.08; 356/442

(56) References Cited

U.S. PATENT DOCUMENTS

| | | | |
|---|---|---|---|
| 4,760,548 | 7/1988 | Baker et al. | 364/718 |
| 5,171,688 | 12/1992 | Hewett et al. | 435/289 |
| 5,512,745 | 4/1996 | Finer et al. | 250/251 |
| 5,674,743 | * 10/1997 | Ulmar | 435/288.7 |

FOREIGN PATENT DOCUMENTS

| | | |
|---|---|---|
| 666473 | 8/1995 | (EP) . |
| 723146 | 7/1996 | (EP) . |
| WO 94/16313 | 7/1994 | (WO) . |
| WO 96/22521 | 7/1996 | (WO) . |
| WO 96/22531 | 7/1996 | (WO) . |
| WO 96/27798 | 9/1996 | (WO) . |

\* cited by examiner

Primary Examiner—Georgia Epps
Assistant Examiner—Richard Hanig
(74) Attorney, Agent, or Firm—James C. Lydon

(57) ABSTRACT

A method for quantitatively measuring nucleic acid amplification reactions, especially the polymerase chain reaction, employing microparticles as hybridization solid phase, a probe sequence labeled with a fluorescent label and a fluorescence detection system which is based on two-photon fluorescence excitation, contacting all the amplification reaction components and the solid phase simultaneously in a closed cuvette, performing the amplification reactions in the same cuvette, focusing a two-photon exciting laser beam into the cuvette during the amplification cycles and measuring the fluorescence signal emitted by the microparticles from one particle at a time when they randomly float through the focal volume of the laser beam. The features of this invention allow a method and device for performing a fast quantitative nucleic acid amplification assay of single or multiple target sequences in a very small closed sample volume.

8 Claims, 3 Drawing Sheets

METHOD AND A DEVICE FOR MONITORING NUCLEIC ACID AMPLIFICATION REACTIONS

METHOD AND A DEVICE FOR MONITORING NUCLEIC ACID AMPLIFICATION REACTIONS

This application is a continuation-in-part of pending application Ser. No. 09/297,578, filed May 5, 1999.

BACKGROUND OF THE INVENTION

Amplification of minute amounts of nucleic acid sequences by techniques such as the polymerase chain reactions is an established method, widely used for example in routine diagnostics and research laboratories. A standard nucleic acid amplification reaction consists of repeatedly copying a target sequence and the produced copies generating an exponential multiplication process of the target sequence. After several tens of multiplication cycles the nucleic acid sequences can be detected and their amount measured by using a label that attaches to the copied sequence and detecting that label. Commonly used labels are fluorescent molecules, radioisotopes and chemiluminescent molecules.

The most common nucleic acid amplification reaction is the polymerase chain reaction (PCR). PCR consists of repeatedly cycling the reaction volume through different temperatures to 1) denaturate the formed nucleic acid double stranded helixes, 2) anneal short nucleic acid sequences called primers to the now single stranded halves of the double helix at the ends of the portion of the nucleic acid sequence to be amplified, 3) elongate the still partially single stranded nucleic acid sequences with the help of a special enzyme such as the Taq DNA polymerase, 4) return back to denaturation step of the cycle.

The method according to this invention refers to those fluorometric nucleic acid amplification assays where one of the reacting nucleic acid sequences is attached to microparticles serving as a solid matrix. The solid matrix attached sequence combines with its counterpart from the amplification reaction solution. Detection of the amount of the solid matrix bound nucleic acid sequence follows by detection of increased or decreased fluorescence.

A special problem of the nucleic acid amplification reactions is related to their extreme sensitivity. Any carry-over or any false matching sequence is amplified along with the desired target sequence. These non-target sequences are introduced either as impurities or by miscombination during annealing phases. To avoid such problems the amplification factor should therefore be kept as low as possible and the reaction volume closed throughout the amplification cycles.

Some applications require the quantification of the target. The procedure includes observing the number of cycles as well as the amplification rate from cycle to cycle. Quantitative determination of the target can only be performed during the exponential growth rate of the target product, i.e. when the number of cycles is as low as possible. This type of assay can only be performed effectively if the measurement takes place directly from the reaction volume, i.e. the assay is homogeneous. Most common techniques using fluorescence, radioisotopes or chemiluminescence require stopping of the reaction and performing incubation and washing steps for the assay. Such assays are not optimally suited for quantification purposes since all the steps must be predetermined - precision and dynamics of the quantification is compromised. A known homogeneous assay type suitable for direct measurement of amplification process bases on the use of fluorescence resonant energy transfer (FRET). In this method as a nucleic acid double helix is formed, two labels being parts of the sequence are brought into close proximity. The first, normally fluorescent label is quenched by the second label. The quenching only takes place in close proximity and thus free labels are not affected. The amount of formed amplification product is measured from the drop in total fluorescence signal. An inherent problem in this technique is it's yet low sensitivity thus necessitating a relatively high number of amplification cycles to be performed.

In PCR the sample is cycled through different temperature steps. The speed of reaching each of the temperature levels determines the speed at which the amplification reaction advances. This in turn is directly dependent on the volume of the sample; smaller samples are preferable from this kinetic point of view. Contrary to this kinetic requirement is the detection sensitivity where conventional detection technologies benefit from larger volumes.

There is a constant need for simpler, faster, more cost-effective and more sensitive nucleic acid sequence amplification analyses. The new nucleic acid sequence amplification assay method of the present invention using fluorescent labels enables the direct and sensitive measurement of the amplification reaction without separation and washing steps enabling the on-line monitoring of amplification process in a closed cuvette. The new method has no practical volume limits and is thus well suited for very small volumes. The new method is particularly well suited for using together with the PCR amplification. Further the new method is suited for multiparametric determination of amplification products. Different sequences and control sequences may be monitored from the same amplification volume.

Two-Photon Excitation

Two-photon excitation is created when, by focusing an intensive light source, the density of photons per unit volume and per unit time becomes high enough for two photons to be absorbed into the same chromophore. In this case, the absorbed energy is the sum of the energies of the two photons. According to the concept of probability, the absorption of a single photon in a dye, is an independent event, and the absorption of several photons is a series of single, independent events. The probability of absorption of a single photon can be described as a linear function as long as the energy states that are to be excited are not saturated. The absorption of two photons is a non-linear process. In two-photon excitation, dye molecules are excited only when both photons are absorbed simultaneously. The probability of absorption of two photons is equal to the product of probability distributions of absorption of the single photons. The emission of two photons is a thus a quadratic process.

The properties of the optical system used for fluorescence excitation can be described with the response of the system to a point-like light source. A point-like light source forms, due to diffraction, an intensity distribution in the focal plane characteristic to the optical system (point spread function). When normalized, this point spread function is the probability distribution of how the photons from the light source reach the focal area. In two-photon excitation, the probability distribution of excitation equals the normalized product of intensity distributions of the two photons. The probability distribution thus derived, is 3- dimensional, especially in the vertical direction, and is clearly more restricted than for a single photon. Thus in two-photon excitation, only the fluorescence that is formed in the clearly restricted 3-dimensional vicinity of the focal point is excited.

When a dye is two-photon excited the scattering of light in the vicinity of the focal point and from the optical components, is reduced remarkably compared to normal excitation. Furthermore, two-photon excitation decreases the background fluorescence outside the focal point, in the surroundings of the sample and in the optics. Since the exciting light beam must be focused onto as a small point as possible, two-photon excitation is most suitable for the observation of small sample volumes and structures, which is also the case in the method according to this invention.

The advantage of two-photon excitation is also based on the fact that visible or near-infrared (NTR) light can, for example, be used for excitation in the ultraviolet or blue region. Similarly, excitation in the visible region can be achieved by NTR light. Because the wavelength of the light source is considerably longer than the emission wavelength of the dye, the scattering at a wavelength of the light source and the possible autofluorescence can be effectively attenuated by using low-pass filters (attenuation of at least 10 orders of magnitude) to prevent them from reaching the detector.

Since in two-photon excitation the density of photons per unit volume and per unit time must be very high in order to make two photons to be absorbed into the same chromophore, it is useful to use lasers which generate short pulses with high repetition rate. A practical laser for two-photon excitation is for example a passively Q-switched Nd:YAG laser with a pulse length of 1 ns.

OBJECT AND SUMMARY OF THE INVENTION

The object of this invention is related to an improved and more sensitive homogeneous nucleic acid amplification monitoring method and device, especially for use with the PCR, employing microparticles as solid phase. Another object of this invention is to provide a multiparametric monitoring method and device to accommodate the needs of the nucleic acid amplification assays, in particular the reduction of the reaction volume. This invention also relates to a homogeneous assay system for end-point detection of amplification results, such as PCR products, when amplification is performed in a separate device and the measurement of the product is carried out by means of the present invention. Another object of this invention is to provide a homogeneous nucleic acid hybridization assay and measurement system for applications where amplification of the nucleic acid is not required. This can also be understood as a special case of amplification product detection at zero amplification cycles. In the method according to the present invention, the amplification reaction product is detected by use of a fluorescent label that attaches together with the target sequence to the surface of a microparticle. The fluorescence excitation is based on two-photon excitation. Since two-photon excitation is restricted to a diffraction limited focal volume, only one microparticle at a time fits in the two-photon excited focal volume, and the free labels outside the focal volume do not contribute any significant background signal.

The method and device referred to above and described in patent publication WO 96/22531, allows a separation free nucleic acid hybridization assay for very small sample volumes but the methodological and instrumental set-up of the assay system in the presented form requires a complicated microfluidics system and is not suited for on-line monitoring of the nucleic acid amplification reactions. The objective of this invention is to further improve said method and device to facilitate the needs of nucleic acid amplification assays. In order to make the method applicable to on-line monitoring of the amplification assays, especially the PCR, the improvement of this invention is relative to following design requirements:

Simplification of the liquid handling system enables the measurement of amplification reactions directly from the reaction cuvette as the amplification advances. This is especially important in quantitative analysis using PCR.

The assay should be fast. This means that the microparticles should be measured at high rate and the signal obtained from each particle should be high enough.

The assay should enable the use of a closed sample cuvette to avoid false results due to contamination.

The crucial point of the method of this invention is that the assay can simply be performed by focusing the laser beam directly to the reaction suspension and the amount of amplification product annealing on the surface of the microparticles can be monitored without the need of complicated liquid handling and flow systems. This invention leads to a remarkable methodological simplification but it also allows many other useful features which satisfy the assay requirements defined above and which will be discussed later in this text.

The method of the present invention is related to measuring nucleic acid amplification reactions. The method employs microparticles as target binding solid phase to which a label molecule is bound or incorporated. The label may be on a separate probe sequence, or it may be incorporated into the amplified product as a labeled primer sequence or as labeled nucleotides. A sequence referred to as 'probe' is an oligo nucleic acid sequence, complementary to a sequence within the amplification target or product. The probe is not participating in the amplification reaction as a primer.

Another possibility is to use intercalating DNA dyes to detect microparticle bound double stranded DNA. The detection of the amplification product from the microparticle surface is performed by the use of a fluorescent label and two-photon excitation.

The fluorescent probe, primer, nucleotide, or intercalating dye is attaching to the microparticle surface to indicate the level of amplification for example but not limited by the following means:

1)

One of the primers (later called as "first") is attached on the microparticle and the second primer is free in the solution. It may be beneficial to include a limited amount of the bound first primer also in the liquid phase for more efficient initiation of the reaction.

During amplification, the bound primers, including the microparticle bound first primer, are elongated.

A fluorescently labeled probe complementary to the nucleic acid strand elongated form the first primer anneals to the elongated strand during the annealing phase of the reaction, making the microparticles fluorescent at the time.

During the subsequent elongation phase, the probe is displaced by the proceeding polymerase, and the fluorescence form the microparticles returns to the baseline.

2)

The first primer is attached on the microparticle and the second primer is fluorescently labeled.

During amplification, the primers are elongated and are incorporated into newly formed nucleic acid strands.

During later annealing phases, labeled, elongated and non-elongated second primer anneal with the elongated first primer bound to the microparticle and make the microparticles fluorescent until the denaturation phase drives the strands apart.

3)

One of the primers is attached on the microparticle and the second primer is free in the solution.

Alternatively, both primers are attached on the microparticle and only a limited amount of primers are free in the solution.

Labeled nucleotides are included in the reaction mixture.

During amplification, these nucleotides become incorporated into the newly formed strands.

Strands extending from the bound primers make the microparticles permanently fluorescent and during annealing and elongation phases the fluorescence is increased.

4)

One of the primers is attached on the microparticle and the second primer is free in the solution.

A nucleic acid double helix intercalating dye is included in the reaction mixture.

Preferentially, the fluorescence of the dye is very weak when the dye is free in the solution and is greatly enhanced when the dye is bound to a double stranded nucleic acid molecule. Such dyes are available and well known to one knowledgeable of the art.

The double stranded nucleic acid formed on the microparticles during amplification binds dye from the solution and enables the nucleic acid double helix and the microparticle fluorescent until the denaturation phase drives the strands apart.

5)

Primers are free in the solution and labeled primers or nucleotides are used to incorporate label in the amplification product.

A separate probe sequence(s) on the surface of a microparticle is used to capture one or both of the strands after the denaturation phase, and the microparticles become fluorescent.

The crucial point of this invention is the use of two-photon excited fluorescence signal to detect the formation of nucleic acid amplification products. A two-photon exciting laser beam is focused into the reaction suspension and the fluorescence emission is measured from the single microparticles when they randomly float through the focal volume of the laser beam.

The device needed for carrying out the method of the present invention can perform measurement continuously from the amplification reaction. The device incorporates a means for generating a two-photon exciting laser beam, which can be focused into the reaction suspension for measuring the fluorescence emission from the single microparticles when they randomly float through the focal volume of the laser beam.

DETAILED DESCRIPTION OF THE INVENTION

PREFERRED EMBODIMENTS

Figure 1:
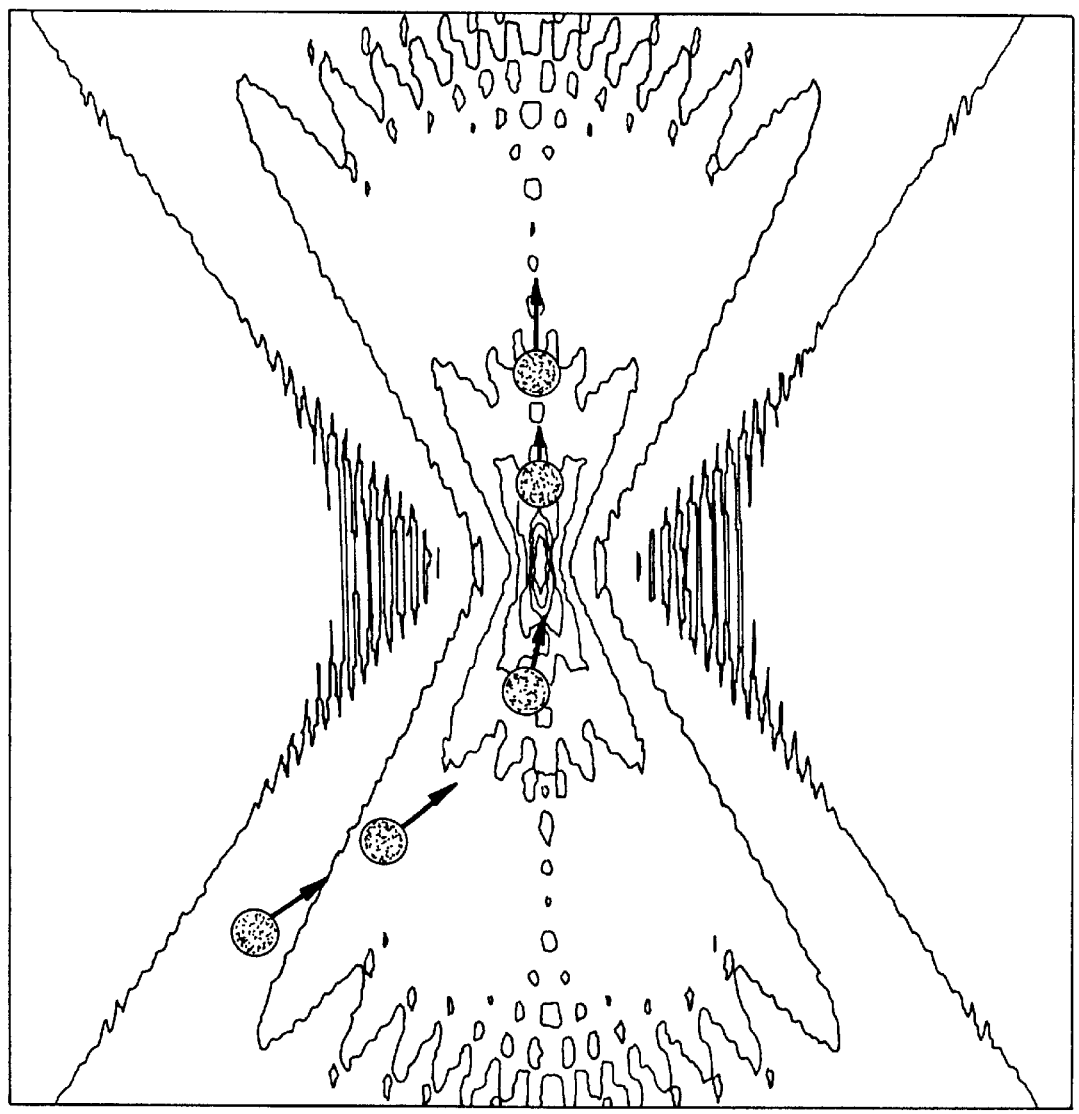
FIG. 1 shows the migration path of a particle through a laser beam's ellipsoid-shaped two-photon excitation volume, with the laser beam being focused through an objective lens having a numerical aperture of 0.65, the laser intensity profile being sown in the two dimensional case, and the vertical axis being the direction of the laser beam.

The efficiency of the measurement can be improved by active trapping techniques which means that the microparticles are trapped for the period of fluorescence detection with an optical trap. The trap is preferably performed with same laser beam as sued for the two-photon fluorescence excitation. The duty cycle of trapping can be improved by a mechanical or optical scanner, which moves the sample containing the microparticles in relation to the focal point or deflects the focusing beam with respect to the sample. The scanner movement can be controlled by a signal obtained from a confocal detector measuring light scattering or reflection from the microparticles and the speed of scanning is reduced for the period of measuring the fluorescence emission.

According to a preferred embodiment, the device comprises an objective lens and a laser that can be focused into the reaction volume through said objective lens for performing an optical trap for the microparticles and the laser power and the numerical aperture of the objective lens have been optimized for performing the optical trap within the two-photon excitation focal volume. The device can incorporate a mechanical or optical scanner, controlled by a trigger signal obtained from the light scattering detector, for moving the sample containing the microparticles in relation to the focal point or deflecting the focusing beam with respect to the sample and a control system for reducing the scanning speed for the period of fluorescence detection. The light scattering detector is confocal with the laser beam.

Since the focal volume of the laser beam is restricted by diffraction, the light beam is focused only on a single microparticle at a time. Due to movements of the suspension, the microparticles randomly move in and out of the focal volume. The label on the surface of each microparticle, which float into the focal volume, is excited by two-photon absorption and its fluorescence emission is measure with a photon detector. The signal relative to the photon count rate obtained from the detector is dependent on the amount of amplification products. By following the signal change during amplification products. By following the signal change during amplification cycling, it is possible to obtain information of the amount of target sequences in the original sample as well as of the efficiency and specificity of the amplification reaction. Since microparticles are observed individually multiple target sequences, possibly including a control sequence, can be observed in a single amplification volume as described in patent publication WO 96/22531 by the inventors.

The method can be carried out, but is not limited to, e.g. as follows:

One of the primer sequences is immobilized to the microparticle surface prior to amplification cycles.

Prior to amplification a second primer, one or more of the nucleotides, or a probe sequence is labeled with a fluorescent label.

Instead of labeled reactants, an intercalating dye with strong binding affinity to double stranded nucleic acid helix and enhancement of fluorescence when bound, can be used.

As an alternative to solid phase primer, a probe sequence can be immobilized to the microparticle surface and primers or one or more of the nucleotides is labeled with a fluorescent label.

An excess amount of primers and nucleotide bases together with the target sequence sample are introduced to the PCR suspension cuvette.

An exactly determined amount of properly prepared microparticles to detect a single or multiple types of amplification products are introduced to the same cuvette.

In case of one of the primers been bound to the solid it may be advantageous to add a limited supply of the same primer in free form to facilitate faster reaction times in the early cycling steps.

Possible control samples and control microparticles are added.

The cuvette is closed after introducing all the necessary components.

The PCR reaction cycling is started and the fluorescence response from the microparticles measured in between the cycles.

Amplification factor is determined from the registered signals.

The quantity of the target or multiple targets is determined from the amplification factor and the number of cycles.

A calculation example for the sensitivity of the method of the invention is given in example 1. Example 2 shows a hybridization assay performed according to the method and device of the invention.

Direct Measurement of Amplification Product Formation in the Reaction Volume

Monodispersive shperical microparticles with diameter of 0.01–100 micrometer can be produced from appropriate polymer, glass and other optically transparent material so that they are well suited for water suspensions. Suitable surface properties can be provided for binding of nucleic acid sequences.

The use of monodispersive microparticles as the solid phase in this nucleic acid amplification assay ensures a rapid cycling of the amplification reaction. Since in the reaction, which occurs on the surface of the microparticles, the average distance between the reaction components is very small, the reaction equilibrium is reached quickly. If one of the reaction primers is attached to the microparticle surface the reaction rate in the early stages of the amplification can be further enhanced by the use of a limited unbound supply of the same primer; as the exponential process advances the free primer is exhausted and the primers from the microparticle surfaces replace their function, preferably at the detection limit of the measuring system.

The microparticles that function as solid phase are in a continuous random movement in the amplification suspension. This movement, called diffusion, is caused by thermal vibrational forces, and is enhanced by the thermal cycling in PCR amplification. As course of the diffusion, the particles randomly float through the two-photon excitation focal volume and a signal that is proportional to the amount of the fluorescent label on the surface of the microparticle, is registered. The duration of the fluorescence signal depends on the transit time, i.e. the time a microparticle remains in the focal volume. The expected duration of the transit time for 3 micrometer particles as calculated on the basis of the diffusion theory, is in the order of one millisecond.

We have observed, however, that when the microparticles are let randomly float through the focal volume by free diffusion, the transit time can be in the order of 300 ms for 3 micrometer particles. This led to a discovery that the strong laser beam that was needed for two-photon excitation, functions as an optical trap either in two or three dimensions depending on the laser power and on the numerical aperture of the objective lens. The three-dimensional trap allows a long trapping time until the particle is released from the trap. This can be accomplished for example by switching off the laser for a short period of time.

The optical trapping effect is based on the radiation pressure and repulsion forces caused by the laser radiation. The direction and strength of the trapping forces depend on the size, shape and refractive index of the particle. In addition the wavelength of the radiation as well as the light absorbance and reflectance of the particle play an important role. A laser beam with very tight focus will form trapping forces both in axial and lateral directions. A laser beam with a smaller focusing angle (low numerical aperture of the focusing lens) will form trapping forces in lateral direction and propulsion forces in axial direction. In this later case, when a microparticle is floating into the vicinity of the focal volume, it will fall into the two dimensional potential well inside the focal volume and it remains there until it is pushed out from the focal volume by the propulsion forces. The theory and applications of the optical trap have been described in the literature (Ashkin A., Phys. Rev. Lett. 24(4):156, 1970 and Ashkin, A., Dziedzic, J. M., Bjorkholm, J. E., and Chu, S. Opt. Lett. 11(5):288, 1986).

FIG. 1 presents a contour model for the double funnel shaped laser intensity profile (point spread function) around the focal point in the two dimensional case. The vertical axis is the direction of the laser beam. The contours indicate the relative intensity distribution. The model has been calculated on the basis of the theory as presented by Richards & Wolf 1959 that can be found for example in: Stamnes, J. J. (1986), Waves in focal regions: Propagation Diffraction and Focusing of Light, Sound and Water Waves, pp. 461-. Bristol, England: Adam Hilger Imprint by IOP Publishing Limited. The dimension of one scale unit is 4 micrometer. The numerical aperture of the objective lens for this model is 0.65. The radiation pressure exposed to a particle is sucking the particle into the ellipsoid shaped two-photon excitation volume and then pushing it out in direction of the vertical axis. FIG. 1 shows how a 3 micrometer particle will migrate through the funnel and how it moves through the center of the focal point and how it remains a relative long time under two-photon excitation. The use of the two dimensional trap leads in any case to a much longer average transit time than if the particle was affected only by transversal diffusion. Consequently the total number of photon counts during the transit time is larger than without trapping effect.

In our experiment, same laser functioned for two-photon excitation of the fluorescent dye and as a means for a two dimensional optical trapping of the microparticles. In this experiment we used a passively Q-switched Nd:YAG laser producing 30 mW at 1064 nm wavelength and objective lenses of numerical aperture of 0.65 to 0.8.

The trapping effect in the context of this invention was found very important since it increases the total counts of detected photons. Since the microparticles remain a longer time in the focal volume and a larger portion of randomly moving particles will float through the center of the focal point, the variance of the counts obtained from different particles is smaller.

Simplification of the Liquid Handling System

Another possibility offered by concept of this invention is the simplification of the liquid handling system. This can be accomplished simply by focusing the two-photon exciting laser beam into the reaction volume through a transparent window of the reaction cuvette. Thus, a fluorescence signal is obtained when a microparticle randomly floats in and out of the focal volume either due to diffusion or liquid movement.

The amplification reaction well array can be made for carrying a large number of closed samples in very small volumes. The detection system based on two-photon excitation allows very small reaction volumes without any loss of performance and consequently the smallest practical reaction volume is limited by the dispensing of the sample rather than by detection. It is obvious that a reaction volume of the order of 1 microliter would be practical form various points of view. Such a small volume can be dispensed in a shallow well in a flat substrate and this substratum can incorporate a large number of such wells in an array. Such wells can be sealed for the duration of amplification reactions, for example by a foil or by a cap. Temperature cycling of the small volumes is fast.

Dispensing of microvolumes can be performed for example using droplet generators, which are based on the use of piezoelectric actuators. A typical droplet generator currently commercially available can make 0.1–1 nl droplets with 1–2 kHz frequency.

Increasing the Particle Rate

Many applications of the nucleic acid amplification assays involve a large number of samples. Each sample should further be measured several times in order to monitor the advancing of the amplification reactions. A requirement for high sample throughput is a high yield of signal and a good statistical precision in a short time. When applied to the method of this invention, these requirements lead to the demand of a high particle rate and a short counting time.

In the amplification assay system according to this invention the microparticles may randomly float, for example due to diffusion, into the focal volume of the laser beam. The rate of microparticles floating into the focal volume depends on microparticle concentration. To speed up the measurement, the suspension can be made to move, or the cuvette or any container including the suspension may be stirred or rotated at a desired speed. The faster is the movement, the higher is the rate of particles randomly floating through the focal volume.

The particle rate, the number of particles floating through the focal volume per second, is proportional to the particle concentration. The particle size and concentration in an assay has an optimum depending on the assay performance parameters and it is favorable to use small microparticles and relative low concentrations. Low number of small microparticles facilitates the highest sensitivity detection of the amplification product. On the other hand high sensitivity may compromise reaction rates so the number and size of the microparticles should be adjusted for optimal performance. When using for example 2 micrometer microparticles, the optimum particle concentration for the highest performance is less than $10^7$ particles/ml and this is at least one order of magnitude lower than needed for a reasonable particle rate with free diffusion. The fluorescence emission takes place only during the period when the particles moving across the focal volume and are under two-photon excitation. Small particles move faster than large particles an they remain in the focal volume much shorter time. This lead to a definition of excitation duty cycle, which is the ratio between the total excitation time and the total elapsed time. In the example given above, the duty cycle is in the order of $10^{-2}$, which is very low. Such a low duty cycle means that the counting is active only for a very small fraction of the elapsed time and consequently the number of photon counts remains low and the total counting time, necessary for required statistical precision, is long.

The particle rate can be increased by moving the suspension, or the reaction chamber, in respect to the focal point, or vice versa. The particle rate increases by increasing the speed of the movement. Scanning by up to 100 micrometers/second keeps the 3 micrometer particle in the two-dimensional trap but when increasing the scanning speed, the particle is released from the focal trap. With increased scanning speed, the trapping forces of the optical trap are too small for keeping the particle in the trap because the optical trapping forces cannot resist the viscosity friction forces. Therefore with increased speed the transit time becomes shorter in the same proportion and the duty cycle remains at the same low level.

We have found, however, that the duty cycle can be improved with the active trapping technique. This is accomplished by using an electronically controlled mechanical or optical scanning system for moving the microparticle suspension in relation to the focal point or vice versa. The movement should be fast enough for bringing a new particle into the focal volume much quicker than the diffusion. A feedback from the detector to the scanning system reduces the scanning speed immediately when the signal caused by the microparticle is detected. The scanning speed is reduced for a short period of time only. If using two-dimensional trapping, the scanning speed is reduced for the period of the time equal to the microparticle trapping time in the focal funnel. After this short period the scanning speed is recovered again for finding a new particle.

We have found that by using an optomechanical beam scanner by performing a circular beam scanning movement with a radius of 0.5 mm, the duty cycle can be improved significantly. Optimizing the laser's power and numerical aperture of the objective lens, the transit time can be made shorter and the particle rate higher, respectively.

The optomechanical trapping scanner can be operated with an electromechanical, galvanometric or piezoelectric actuator. The signal for control of the trapping scanner can best be obtained from a scattering detector at the laser wavelength. When using microparticles made of latex or other optically transparent material with high refractive index, the scattering signal is strong. The scattering signal is needed early enough when the microparticle approaches to two-photon excitation focal volume in order to reduce the scanning speed and to allow trapping effect to work. By using a confocal scattering detection system with an appropriate pinhole in front of the scattering detector, it is possible to optimize the size of the spatial scattering response function. In a multiparametric measurement the scanning may also be controlled by the identification signal from the microparticles.

The microphotometric measurement system used for the device of this invention can distinguish optically between the fluorescence emitted from the surface of the microparticles and the fluorescence emitted from the solution surrounding the particles. This resolution capability is based on the fact that in an appropriately diluted reaction suspension, only one microparticle at a time fits in the focal volume. The microparticles concentrate the fluorescently labeled nucleic acid sequences and the concentration of the labels interms of mole/l in the microscopic volume of the microparticle is many order of magnitude higher that that of the free label molecules in the suspension. Consequently the background signal caused by free, labeled nucleic acid sequences is minimal. Optical separation ensures sufficient resolution capability between free and bound fraction without chemical or physical separation.

Combining the features of this invention as described above with the microparticle based amplification assay system allows a method and device for performing quantitative and sensitive nucleic acid amplification, especially PCR assays from very small sample volumes in a close cuvette enabling fast amplification temperature cycling.

Characteristic of this invention is that the need of microfluidics liquids handling is minimized by focusing the laser beam directly into the reaction volume. In addition the microparticle rate was well as the photon count rate can be made high using active optical trapping.

The method and the related device according to this invention can be realized in many different ways. However, an essential feature of this invention is that by directly focusing the laser beam into the reaction suspension a statistically precise measurement result can be obtained in a short period of time because the detection duty cycle can be kept high by active trapping method. The fluorescence detector is activated only for the duration of the laser pulse used for two-photon excitation, which means that photon emissions or thermal noise counts, which occur between excitation intervals, are not measured. Simultaneously, the photon detector can only be activated at the very moment the microparticle hits the focal volume. Information about the position of microparticles at the focal volume is obtained, for example, through scattering and reflection at the laser beam wavelength. A preferable way to measure scattering is to use a confocal set-up The method of this invention, which is based on the use of two-photon excitation, can also be a multiparametric amplification assay as presented in international patent publication WO 96/22531. In this assay, microparticle are divided into many different categories and they are coated with various primers or probe sequences. These categories may contain controls to validate the assay. The manufacturing expenses of the measurement equipment in mind, it is appreciable that he excitation light used to detect particles, and the two-photon excitation of the label, can be performed with the same laser beam using either red or NIR range wavelength.

A specialist in the field appreciates that the different applications of the said invention may vary within the scope of the claims presented in the following section. The fluorescence system for example may be realized by several ways, i.e. by use of fluorescence resonant energy transfer, intercalating dyes, clusters of label molecules or by use of fluorescent nanoparticles.

EXAMPLE 1

In a PCR reaction the target amplification follows the formula $$N=NO*(1+E)^{x}n \quad (1)$$

Where N is the number of product sequences, NO the original amount of target sequences before amplification, E the efficiency of the amplification and n the number of amplification cycles. In a typical PCR situation an efficiency of better than 90% is expected. Also we have determined that under optimized homogeneous assay conditions the described method and device makes it possible to detect minimally 10 bound fluorescent molecules from a single microparticle. Further assuming that a reaction volume of 1 microliter is used it is possible to calculate the number of cycles necessary to amplify a single target sequence by PCR to a detectable level.

Assuming further that we have 5000 microparticles in the assay and that 50% of the produced sequences are bound we can calculate that the minimum number of molecules needed by the detection limit is $$5000 \text{ part} * 10 \text{ molec/part} * 1/50\% = 100\,000 \text{ molecules}$$

From equation (1) we can then calculate:

$$100\,000 \text{ molec} = 1 \text{ molec} * (1+90\%)^{x}n$$

$$n = \log(100\,000) / \log(1.9) = 18$$

Thus minimum of 18 amplification cycles is necessary. All known homogeneous method require typically more than 30 amplification cycles.

EXAMPLE 2

The following assay shows quantitative detection of microparticle bound short nucleic acid sequence by using a probe with fluorescent label.

Particles used in the assay were streptavidin coated spherical microparticles with 3.2 micrometer diameter available form Bans laboratories. A synthetic 20-mer oligonucleotide target with 5'-end biotin was purchased from KEBO Lab. The purpose of the biotin was to direct the oligonucleotide target on the surface of the microparticle through binding with streptavidin. An oligonucleotide analytical probe with 3'-end tetramethylrhodamine (TAMRA) was purchased from Amersham Pharmacia. The probe was a 13 nucleotides long sequence complementary to nucleotides 5–17 of the target sequence. The melting temperature of the probe was 33.1° C. Said components of the assay were diluted in assay buffer containing 50 mM tris-HCl (pH 8.0 at 25° C.), 0.5% bovine serum albumin, 0.5 M NaCl, 0.01% Tween 20, and 10 mM sodium azide.

Figure 2:
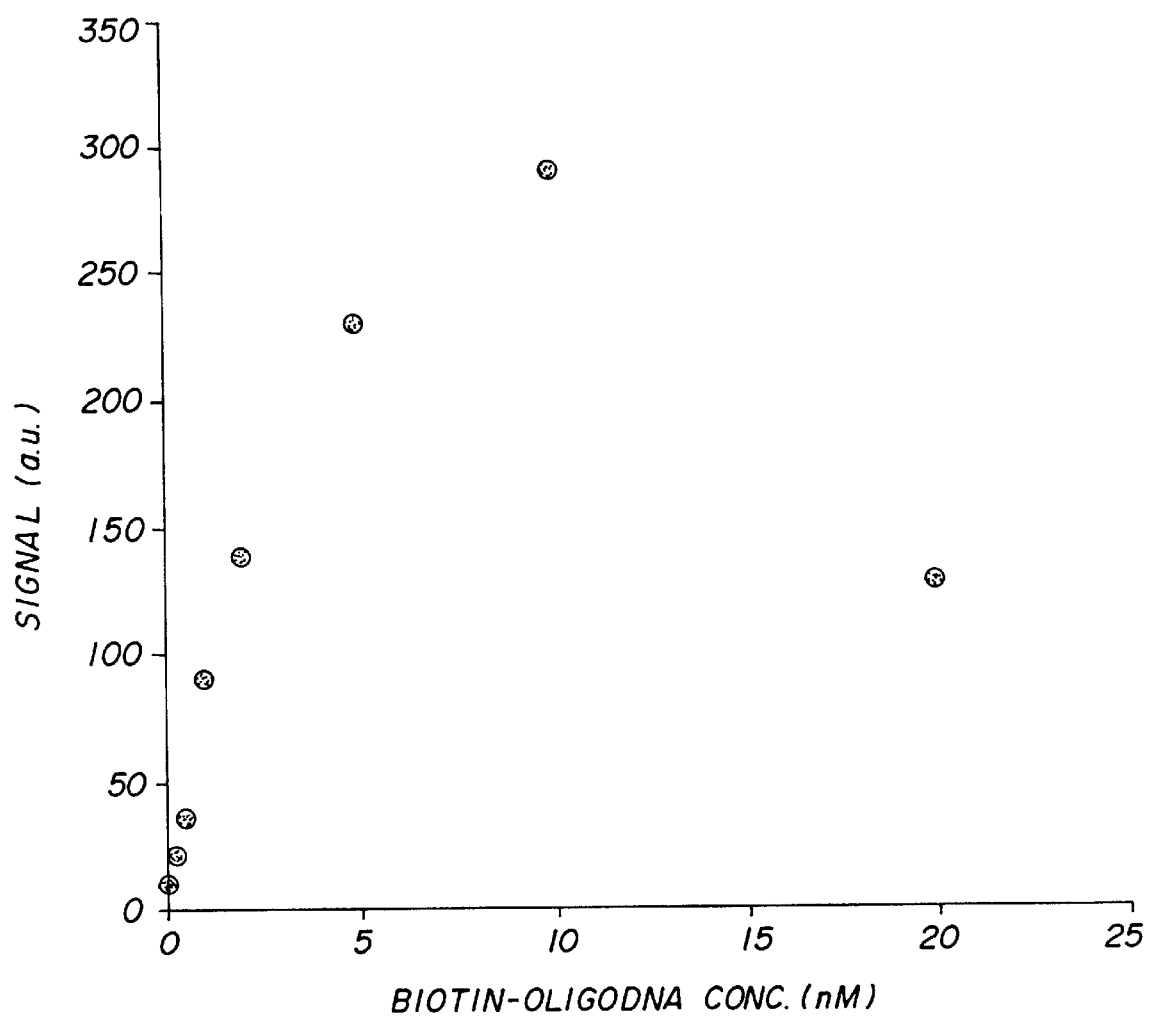
FIG. 2 is a plot of fluorescence detected from oligonucleotides bound to microparticles and labeled with tetramethylrhodamine against concentration.
Figure 3:
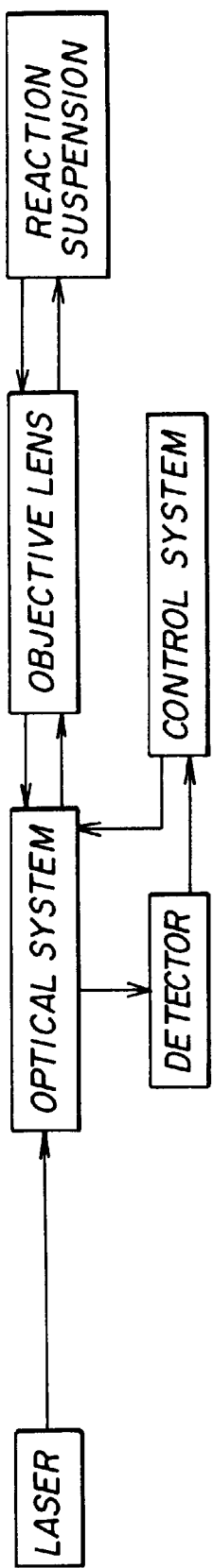
FIG. 3 illustrates a device for monitoring nucleic acid amplification reactions.

A dilution series of biotin-target was prepared to make samples with 0, 0.2, 0.5, 1, 2, 5, 10, or 20 nM final concentration. Each sample of the assay had a total volume of 50 microliter and included 300,000 microparticles and 5 nM TAMRA-probe. The hybridization reaction was carried out overnight at room temperature with rotation mixing and the microparticle fluorescence was measured by the device of the invention. Oligonucleotide target was detected by hybridization with TAMRA-probe in a dose-response manner (FIG. 2). Signal from particles increased up to 10 nM target concentration. The difference in signal from 0 nM and 10 nM target concentration was 28-fold.

We have also observed the following, verifying results:

Streptavidin particles can be coated with the oligonucleotide target in advance.

When microparticles with hybridizing probe were separated by centrifugation and returned to assay buffer without probe, signal from microparticles without target was removed, whereas signal form particles coated with target remained the same.

When coated microparticles with hybridized probe were heated at 50° C., well above the melting temperature, the signal from the microparticles decreased to the level of non-coated microparticles.

What is claimed is:

1. A method for quantitatively measuring a nucleic acid amplification reaction which employs microparticles to bind a nucleic acid sequence labeled with a fluorescent label, said method comprising contacting all nucleic acid amplification reaction components in a single environmentally closed reaction volume;

performing a nucleic acid amplification reaction cycle;

scanning a two-photon excitation focal volume within said reaction volume using a mechanical or optical scanner and a two-photon exciting laser beam which is capable of two-dimensionally optically trapping the microparticles;

momentarily interrupting or reducing the scanning speed of said two-photon excitation volume when said two-photon excitation volume approaches a microparticle randomly located in the reaction volume;

optically trapping said microparticle such that it falls into a two-dimensional potential well crated by said laser beam; and detecting fluorescence emission photon counts from said microparticle.

2. The method of claim 1, wherein movement of said scanner is controlled by a signal obtained from a detector measuring light scattering or reflection.

3. The method of claim 2, wherein an optical set-up for measuring said light scattering or reflection is confocal.

4. The method of claim 1, wherein said nucleic acid amplification reaction comprises a polymerase chain reaction.

5. A device for quantitatively measuring nucleic acid amplification reactions, comprising a laser capable of generating a laser beam of sufficient power to two-photon excite and two-dimensionally optically trap a fluorescent label attached to a nucleic acid sequence bound to a microparticle in a reaction volume;

an optical system for focusing said laser beam through an objective lens to a focal volume within said reaction volume, said objective lens having a numerical aperture optimized for two-dimensionally optically trapping an individual microparticle, said system being capable of scanning said focal volume at a predetermined speed within said reaction volume;

a detector capable of detecting fluorescence emitted from said focal volume; and a control system for momentarily interrupting or reducing said predetermined scanning speed to a second, slower scanning speed when a microparticle is present in said focal volume, thereby allowing said microparticle to be optically trapped for a period of fluorescence detection by said laser beam during said period of fluorescence detection.

6. The device of claim 5, further comprising a light scattering detector which is confocal with said laser beams.

7. The device of claim 6, wherein movement of said scanner is controlled by a trigger signal received from said light scattering detector.

8. The device of claim 6, wherein movement of said scanner is controlled by a trigger signal received from said light scattering detector.

* * * * *

UNITED STATES PATENT AND TRADEMARK OFFICE
CERTIFICATE OF CORRECTION

PATENT NO.    : 6,310,354 B1
DATED         : October 30, 2001
INVENTOR(S)   : Pekka Hanninen and Erkki Soini It is certified that error appears in the above-identified patent and that said Letters Patent is hereby corrected as shown below:

Column 11,
Line 61, change "$(1+E)^{x}n$" to -- $(1+E)^{\wedge}n$ --.

Column 12,
Line 18, change "$(1+90\%)^{x}n$" to -- $(1+90\%)^{\wedge}n$ --

Signed and Sealed this

Thirtieth Day of April, 2002

Attest:

JAMES E. ROGAN
Attesting Officer       Director of the United States Patent and Trademark Office